United States Patent
Tanimoto et al.

(12)

(10) Patent No.: US 6,399,818 B2
(45) Date of Patent: Jun. 4, 2002

(54) PROCESS FOR PRODUCING UNSATURATED ALDEHYDES AND UNSATURATED CARBOXYLIC ACIDS

(75) Inventors: Michio Tanimoto; Tadashi Sento, both of Himeji (JP)

(73) Assignee: Nippon Shokubai Co. Ltd., Osaka (JP)

( * ) Notice: Subject to any disclaimer, the term of this patent is extended or adjusted under 35 U.S.C. 154(b) by 0 days.

(21) Appl. No.: 09/852,705

(22) Filed: May 11, 2001

(30) Foreign Application Priority Data

May 19, 2000 (JP) ........................................ 2000-147156

(51) Int. Cl.⁷ ........................... C07C 51/25; C07C 47/22
(52) U.S. Cl. ..................... 562/546; 502/205; 562/532; 562/537; 568/471; 568/479
(58) Field of Search ................................ 568/479, 471; 562/537, 538, 546, 599, 532; 502/205, 215, 242

(56) References Cited

U.S. PATENT DOCUMENTS

| | | | |
|---|---|---|---|
| 3,801,634 A | 4/1974 | Krabetz et al. | 260/533 N |
| 4,438,217 A | 3/1984 | Takata et al. | 502/205 |
| 4,511,671 A | 4/1985 | Saito et al. | 502/242 |
| 4,837,360 A | 6/1989 | Kadowaki et al. | 562/546 |
| 5,276,178 A | 1/1994 | Onodera et al. | 562/537 |

FOREIGN PATENT DOCUMENTS

| | | |
|---|---|---|
| EP | 304867 | 3/1989 |
| GB | 1330074 | 9/1973 |
| GB | 1390271 | 4/1975 |
| GB | 1444659 | 8/1976 |
| GB | 1529384 | 10/1978 |
| JP | 4324403 | 11/1992 |

*Primary Examiner*—Sreeni Padmanabhan
(74) *Attorney, Agent, or Firm*—Sherman & Shalloway

(57) ABSTRACT

As an improvement in the process for preparing unsaturated aldehydes and unsaturated carboxylic acids through vapor-phase catalytic oxidation of at least one starting compound selected from propylene, isobutylene, t-butanol and methyl-t-butyl ether with molecular oxygen or a molecular oxygen-containing gas, using a fixed bed shell-and-tube type reactor which is filled with shaped catalysts, a process capable of effectively inhibiting occurrence of hot spots or excessive heat generation at the hot spots and producing unsaturated aldehydes and unsaturated carboxylic acids at high yields is provided. This process is characterized in that plural shaped catalysts exhibiting different activity levels are prepared by varying: [I] content of inert component of the shaped catalyst and [II] at least one of the factors (a) occupation volume of the shaped catalyst, (b) kind and/or amount of the alkali metal(s) in the shaped catalyst, and (c) calcining temperature of the shaped catalyst; and which catalysts are filled in each of the reaction tubes in such a manner that the catalytic activity level rises from the reactant gas-inlet side of each reaction tube toward the outlet side.

4 Claims, No Drawings

PROCESS FOR PRODUCING UNSATURATED ALDEHYDES AND UNSATURATED CARBOXYLIC ACIDS

TECHNICAL FIELD TO WHICH THE INVENTION BELONGS

This invention relates to a process for producing unsaturated aldehydes and unsaturated carboxylic acids. More particularly, the invention relates to a process for vapor-phase catalytic oxidation of at least one starting compound selected from propylene, isobutylene, t-butanol and methyl-t-butyl ether (hereinafter these compounds may be referred to as "propylene and the like") to produce corresponding unsaturated aldehydes and unsaturated carboxylic acids. When propylene is used as the starting compound, acrolein and acrylic acid are produced, and when isobutylene, t-butanol or methyl-t-butyl ether is used as the starting compound, methacrolein and methacrylic acid are formed.

CONVENTIONAL TECHNOLOGY

Many improved catalysts for producing unsaturated aldehydes and unsaturated carboxylic acids with high efficiency by vapor-phase catalytic oxidation reaction of propylene and the like were heretofore proposed. For example, Sho 50(1975)-13308A-JP (=GB 1,444,659A) and Sho 50(1975)-47915A-JP (=GB 1,444,659A) disclosed catalysts whose essential components were Mo, Bi, Fe, Sb, Ni, and at least one another element selected from K, Rb and Cs. Sho 64(1989)-56634A-JP (=EP 304,867A) taught catalysts whose essential components were Mo, Bi, Fe and at least an element selected from Ni and Co.; Sho 56(1981)-52013B-JP (=GB 1,330,074A), the catalysts essentially containing Mo, Bi and Fe and at least an additional element selected from Mg, Ca, Zn, Cd and Ba; and Sho 56(1981)-23969B-JP (=GB 1,390,271), catalysts essentially containing Mo, Bi and Fe, and at least one element selected from Group IIA compounds and Group IIB compounds of the periodic table.

Industrial scale production of unsaturated aldehydes and unsaturated carboxylic acids by vapor-phase catalytic oxidation reaction of propylene and the like is subject to a number of problems, one of which is occurrence of local abnormally high temperature spots (hot spots) in the catalyst layers. Because the vapor-phase catalytic reaction of propylene and the like is extremely exothermic, hot spots may occur in the catalyst layers to induce over-oxidation or the excessive heat generation at the hot spots may cause deterioration of the catalyst. In the worst case, a run-away reaction may be induced. In particular, where concentration of starting material or space velocity is increased to raise productivity of the object products, the excessive heat generation takes place to make stable production of the object products difficult.

Various methods have been proposed to control occurrence of such hot spots or the excessive heat generation at the hot spots. For example, methods in which the catalyst at the hot spots was diluted with inert substances [Sho 43(1968)-24403B-JP, Sho 53(1978)-30688B-JP (=U.S. Pat. No. 3,801,634) and Sho 51(1976)-127013A-JP (=GB 1,529,384A)]; methods in which ring-formed catalysts were used [Sho 62(1987)-36739B-JP (=U.S. Pat. No. 4,438,217) and Sho 62-36740B-JP (=U.S. Pat. No. 4,511,671)]; a method in which two or more reaction zones were provided in each reaction tube [Sho 51(1976)-127013A-JP (=GB 1,529,384A)]; a method in which plural catalysts, which were prepared to have different activity levels by varying the amount and/or kind of alkali metals therein, were filled in the reaction tubes in such a manner that the activity level rose from the reactant gas-inlet side toward the outlet side [Sho 63(1988)-38331B-JP (=U.S. Pat. No. 4,837,360)] were included among the proposals.

PROBLEM TO BE SOLVED BY THE INVENTION

However, those known methods have not completely solved the problems pertaining to the hot spots.

Accordingly, therefore, the object of the present invention is to provide a process for effectively inhibiting or controlling occurrence of hot spots or excessive heat generation at the hot spots to enable production of unsaturated aldehydes and unsaturated carboxylic acids at high yields.

MEANS TO SOLVE THE PROBLEMS

We have discovered, after extensive studies, that when plural shaped catalysts exhibiting different activity levels are prepared by varying: [I] content of inert component of the shaped catalysts; and [II] at least one of the factors (a) occupation volume of the shaped catalysts, (b) kind and/or amount of the alkali metal(s) in the shaped catalysts and (c) calcining temperature of the shaped catalysts; and the catalysts are filled in each of reaction tubes in such a manner that the catalytic activity level rises from the reactant gas inlet side toward the outlet side, occurrence of hot spots or excessive heat generation at the hot spots can be effectively controlled, and in consequence unsaturated aldehydes and unsaturated carboxylic acids can be produced at high yields.

Thus, according to the invention, a process for preparing unsaturated aldehydes and unsaturated carboxylic acids through vapor-phase catalytic oxidation of at least one starting compound selected from propylene, isobutylene, t-butanol and methyl-t-butyl ether with molecular oxygen or a molecular oxygen-containing gas, using a fixed bed shell-and-tube type reactor filled with shaped catalysts is provided, which is characterized in that plural shaped catalysts exhibiting different activity levels are prepared by varying at least one of the factors: [I] content of inert component of the shaped catalyst and [II] (a) occupation volume of the shaped catalyst, (b) kind and/or amount of the alkali metal(s) in the shaped catalyst, and (c) calcining temperature of the shaped catalyst; and which catalysts are filled in each of the reaction tubes in such a manner that the catalytic activity level rises from the reactant gas-inlet side of each reaction tube toward the outlet side.

The term, activity level, as used herein is determined based on the conversion of the starting compound (propylene and the like).

WORKING EMBODIMENTS OF THE INVENTION

The active components of the catalyst to be used in the present invention are not critical, so long as they are useful in vapor-phase catalytic oxidation reaction of propylene and the like, to produce the corresponding unsaturated aldehydes and unsaturated carboxylic acids. Whereas, complex oxides which are expressed by the following general formula (1) are particularly suitable:

$$Mo_aW_bBi_cFe_dA_eB_fC_gD_hO_x$$

(wherein Mo is molybdenum; W is tungsten; Bi is bismuth; Fe is iron; A is at least an element selected from cobalt and nickel; B is at least an element selected from phosphorus, antimony, boron, tin, cerium, niobium, lead, chromium and zinc; C is at least an element selected from alkali metal elements; D is at least an element selected from alkaline earth metal elements; and O is oxygen; a, b, c, d, e, f, g, h and x stand for atomic numbers of Mo, W, Bi, Fe, A, B, C, D and O, respectively; where a is 12, b is 0-5, c is 0.1-10, d is 0.1-10, e is 1-20, f is 0-5, g is 0.001-3, h is 0-5, and x is a numerical value determined by state of oxidation of each of the elements).

The complex oxides which are expressed by the general formula (1) are known, and can be prepared by heretofore known methods. More specifically, for example, Japanese Patent No. 2,659,839 (=U.S. Pat. No. 5,276,178) may be referred to.

The inert component to be used in the invention may be any that is inert to the reaction. For example, those generally used as inert carriers, such as silicon carbide, aluminum oxide (alumina), zirconium oxide (zorconia), titanium oxide (titania), silicon oxide-aluminium oxide (silica-alumina) and the like can be used. Of those, alumina and zirconia are conveniently used.

BET specific surface area of such inert substance desirably does not exceed 20 $m^2/g$, preferably ranging 0.1-15 $m^2/g$, inter alia, 0.5-10 $m^2/g$. Where the specific surface area is large, CO and $CO_2$ formation increases to decrease yield of the object products. Average particle diameter of the inert substance desirably does not exceed 200 $\mu m$, preferably ranging 0.1-100 $\mu m$, inter alia, 0.5-80 $\mu m$. Large particle size is detrimental to its blendability with catalytically active components.

Shaped catalysts according to this invention can be prepared, for example, when a complex oxide expressed by the general formula (1) is used as the catalytically active component, by adding an inert substance to the complex oxide at an optional step during the preparation of a shaped catalyst comprising said complex oxide, and mixing it into the system. For example, a shaped solid catalyst can be prepared by a process comprising: adding starting materials containing the constituent elements as expressed in the general formula (1) to an aqueous medium and mixing; adding an inert substance to the resulting slurry; mixing; heating, drying; pulverizing; adding to the system an additive such as ammonium nitrate, cellulose, starch, polyvinyl alcohol, stearic acid and the like which are generally referred to as binders, together with water; kneading the system and thereafter shaping the kneaded mass into desired forms and calcining the same while passing air. In that occasion, as the first condition [I]. the amount of added inert substance is changed and, as the second condition [II], at least one of (a) the occupation volume of the shaped catalyst, (b) kind and/or amount of the alkali metal(s) in the shaped catalyst, and (c) calcining temperature of the shaped catalyst is changed, to provide plural shaped catalysts having different activity levels.

In an alternative method, shaped catalysts can be prepared by: adding starting materials containing the constituent elements as specified by the general formula (1) to an aqueous medium, mixing, heating the resulting slurry, drying, pulverizing, mixing the resulting powder with an inert substance, and then adding thereto an additive such an ammonium nitrate, cellulose, starch, polyvinyl alcohol, stearic acid and the like which are generally known as binders, together with water, kneading the system and shaping the kneaded mass into desired forms, followed by calcining while passing air. Plural catalysts of different activity levels can be prepared in that occasion, by changing the added amount of the inert substance as the first condition [I], and also by changing at least one of the second condition [II], (a) occupation volume of the shaped catalyst, (b) kind and/or amount of the alkali metal(s) in the shaped catalyst, and (c) calcining temperature of the shaped catalyst.

The content of inert substance is variable within the range of 0–80% by weight, preferably within the range of 0–70% by weight.

The term, "occupation volume of the shaped catalyst", as used herein means the apparent volume occupied by the shaped catalyst. Apparent volume signifies the volume including inside cavities of the shaped catalyst. Therefore, when shaped catalyst bodies are spherical or cylindrical, their occupation volumes equal the cubic volumes of the spheres or cylinders. Again, when the shaped catalyst are ring-formed, for example, their occupation volume equals the cubic volumes of the rings plus those of the spaces surrounded inside the rings. Thus, when (A) the shaped catalyst are spherical, their occupation volume is changeable by changing their diameters; (B) when the bodies are cylindrical, by changing their diameter and/or height; and (C) when they are ring-formed, by changing their outer diameter and/or height of the rings. When inside of each reaction tube is divided into plural reaction zones, it is convenient to fill any two adjacent reaction zones with shaped catalysts of differing activity levels, in such a manner that the ratio ($V_1/V_2$) between the occupation volume ($V_1$) of a shaped catalyst filling the reaction zone closer to the reaction gas inlet side and the occupation volume (V2) of another shaped catalyst filling the reaction zone closer to the reaction gas outlet side falls within the range of 1.2/1–64/1, preferably 1.3/1–27/1.

The amount of alkali metal is variable within the range of, for example, the atomic ratio specified by the general formula (1). The calcining temperature also is variable within a range of 300–650° C., preferably 400–600° C. While the calcination time is not subject to any critical limitation, it normally ranges 1–24 hours, preferably 3–12 hours.

Form of the shaped catalyst according to the invention is subject to no critical limitation, which may be any of granules, pellets, spheres, cylinders, rings and the like.

Apparatus and conditions for practicing the vapor-phase catalytic oxidation reaction of the present invention are not critical. As the reactor, a generally used fixed bed reactor is used, and each of the reaction tubes in that reactor is divided into plural reaction zones, normally two or three, and the zones are filled with the shaped catalysts of different activity levels in such a manner that the activity level rises from the inlet side toward the outlet side of the reaction gas The reaction may be performed under those conditions that are generally selected for preparation of unsaturated aldehydes and unsaturated carboxylic acids through vapor-phase catalytic oxidation reaction. For example, the reaction is performed by contacting a gaseous mixture comprising 1–15 volume % of gaseous starting compound, i.e., propylene and the like (at least one compound selected from propylene, isobutylene, t-butanol and methyl-t-butyl ether), 1–10 volume % per volume % of the gaseous starting compound of molecu ar oxygen and the balance of an inert gas (e.g., nitrogen, carbon dioxide, steam or the like) serving as the diluent, with the shaped catalysts of the invention at temperatures ranging 250–450° C. under pressures ranging 0.1–1 MPa and at space velocities ranging 300–5000 $h^{-1}$ (STP). While nitrogen, carbon dioxide, steam or the like can be used as the inert gas, use of steam is advantageous for improving yields of the object products, because steam has an effect of inhibiting formation of side products.

EFFECT OF THE INVENTION

According to the process of this invention, occurrence of hot spots or excessive heat generation at the hot spots can be effectively inhibited, and in consequence the intended unsaturated aldehydes and unsaturated carboxylic acids can be obtained at high yield.

EXAMPLES

Hereinafter the present invention is explained more specifically, referring to Referential Examples, Working Examples and Comparative Examples. Content of the inert component, conversion of the starting compound, total selectivity for unsaturated aldehyde and unsaturated carboxylic acid, and total one-pass yield of unsaturated aldehyde and unsaturated carboxylic acid as given in those Examples are defined as follows when, for example, propylene is used as the starting compound.

Content of inert component (%) =

$$\frac{(\text{weight of inert component})}{(\text{weight of catalytically active component} + \text{weight of inert component})} \times 100$$

Propylene conversion (mol %) =

$$\frac{(\text{mol number of reacted propylene})}{(\text{mol number of supplied propylene})} \times 100$$

Total selectivity (mol %) =

$$\frac{(\text{total mol number of formed acrolein and acrylic acid})}{(\text{mol number of reacted propylene})} \times 100$$

Total one-pass yield (mol %) =

$$\frac{(\text{total mol number of formed acrolein and acrylic acid})}{(\text{mol number of supplied propylene})} \times 100$$

Referential Example 1

Preparation of Catalyst

In 1 liter of ion-exchange water, 687 g of cobalt nitrate, 412 g of nickel nitrate and 191 g of ferric nitrate were dissolved, and 229 g of bismuth nitrate was dissolved in aqueous nitric acid solution composed of 50 ml of conc. nitric acid and 200 ml of ion-exchange water. Separately, 1000 g of ammonium paramolybdate and 64 g of ammonium paratungstate were added to 3 liters of hot ion-exchange water, and dissolved under stirring. Into the resultant aqueous solution those separately prepared aqueous solutions were added dropwise and mixed, followed by addition of an aqueous solution of 4.8 g of potassium nitrate in 50 ml of ion-exchange water. Thus obtained slurry was heated under stirring to evaporate off the steam to dryness. The solid matter obtained upon further drying was pulverized, and the resulting powder was mixed with suitable amounts of ammonium nitrate and water, together kneaded and shaped into rings of each 6 mm in outer diameter, 2 mm in inner diameter and 6 mm in height. The rings were calcined at 480° C. for 8 hours while passing air, to provide shaped catalyst (1). The metallic elementary composition (by atomic ratios, excepting oxygen, as in all of the hereafter given compositions) of the shaped catalyst (1) was as follows:

The conditions [I] and [II] selected for preparation of the shaped catalyst (1) were as follows:

[I] content of inert component: 0 wt %

[II] (a) occupation volume:

$$170 \text{ mm}^3 \left[ = \pi \left( \frac{6 \text{ mm}}{2} \right)^2 \times 6 \text{ mm} \right]$$

[II] (b) atomic ratio of alkali metal atoms (to $Mo_{12}$): 0.1

[II] (c) calcining temperature: 480° C.

Oxidation Reaction

Into a stainless steel reactor of 25 mm in inner diameter which was filled with 400 ml of the shaped catalyst (1), a gaseous mixture of 5 volume % of propylene, 10 volume % of oxygen, 20 volume % of steam and 65 volume % of nitrogen-containing inert gas was introduced at a space velocity (SV) of 1500 h$^{-1}$, and subjected to the oxidation reaction under the conditions of entrance pressure 0.22 MPa and reaction temperature 300° C. The results were: propylene conversion, 99.3%; selectivity for acrolein and acrylic acid, 93.6%; and yield of acrolein and acrylic acid, 92.9%.

Referential Example 2

Using an alumina powder having a BET specific surface area of 1 m$^2$/g and an average particle diameter of 55 μm, ring-formed shaped bodies of 6 mm in outer diameter, 2 mm in inner diameter and 6 mm in height were prepared by a method similar to that practiced in Referential Example 1. Subsequently, oxidation of propylene was conducted under identical reaction conditions with those used in Referential Example 1, except that the shaped catalyst (1) was replaced by above alumina shaped bodies. It was in consequence confirmed that the propylene conversion was not higher than 0.3% and no substantial reaction took place.

Referential Example 3

The powder which was obtained following the method of Referential Example 1 was mixed with 1900 g of an alumina powder having a BET specific surface area of 1 m$^2$/g and an average particle diameter of 55 μm. The resultant mixture was kneaded under addition of adequate amounts of ammonium nitrate and water, and shaped into rings of each 6 mm in outer diameter, 2 mm in inner diameter and 6 mm in height, which were calcined at 500° C. in an air stream for 8 hours to provide shaped catalyst (2).

Referential Example 4

Referential Example 3 was repeated except that no alumina powder was used, to provide shaped catalyst (3).

Referential Example 5

Into 1 liter of ion-exchange water, 687 g of cobalt nitrate, 412 g of nickel nitrate and 191 g of ferric nitrate were dissolved; and 229 g of bismuth nitrate was dissolved in an aqueous nitric acid solution composed of 50 ml of conc. nitric acid and 200 ml of ion-exchange water.

Separately, 1000 g of ammonium paramolybdate and 64 g of ammonium paratungstate were added to 3 liters of heated ion-exchange water and dissolved under stirring. Into this aqueous solution those two aqueous nitrate solutions were added dropwise and mixed, followed by addition of an aqueous solution of 4.6 g of cesium nitrate in 50 ml of ion-exchange water, and by further addition of 1590 g of an alumina powder having a BET specific surface area of 1 m$^2$/g and an average particle diameter of 55 μm. Thus obtained slurry was heated under stirring to evaporate off the steam to dryness. The solid matter obtained upon further drying was pulverized, and the resulting powder was mixed with suitable amounts of ammonium nitrate and water, together kneaded and shaped into rings of each 6 mm in outer diameter, 2 mm in inner diameter and 6 mm in height. The rings were calcined at 480° C. for 8 hours while passing air, to provide shaped catalyst (4).

Referential Examples 6–12

Referential Example 5 was repeated except that the amount of the alumina powder, kind and/or the amount of alkali metal nitrate, shape of the catalyst and the calcining temperature of the shaped catalyst were varied for each run as indicated in Table 1, to provide shaped catalysts (5)-(11).

Referential Example 13

Referential Example 3 was repeated except that the amount of alumina powder was changed to 865 g and the dimensions of the rings were changed to 9 mm in outer diameter, 2 mm in inner diameter and 9 mm in height, to provide shaped catalyst (12).

The metallic elementary compositions, contents of inert substance, shapes and calcining temperatures of shaped catalysts (1)-(12) as obtained in Referential Examples 1–13 are tabulated as Table 1.

TABLE 2-continued

| | Shaped Catalyst | Propylene Conversion (mol %) | Selectivity for Acrolein and Acrylic Acid (mol %) | Yield of Acrolein and Acrylic Acid (mol %) |
|---|---|---|---|---|
| Referential Example 6 | (5) | 88.5 | 94.8 | 83.9 |
| Referential Example 7 | (6) | 82.7 | 96.0 | 79.4 |
| Referential Example 8 | (7) | 85.6 | 94.4 | 80.3 |
| Referential Example 9 | (8) | 80.4 | 96.5 | 77.6 |
| Referential Example 10 | (9) | 85.3 | 95.0 | 81.0 |
| Referential Example 11 | (10) | 78.9 | 96.7 | 76.3 |
| Referential Example 12 | (11) | 79.6 | 97.0 | 77.2 |
| Referential Example 13 | (12) | 81.3 | 96.4 | 78.4 |

Example 1

The stainless steel reaction tube of 25 mm in inner diameter was filled, from the reaction gas inlet side toward the outlet side, with 500 ml of shaped catalyst (2) and then with 1,000 ml of shaped catalyst (1). A gaseous mixture of 10 volume % of propylene, 16 volume % of oxygen, 5 volume % of steam and 69 volume % of nitrogen-containing inert gas was introduced into the reaction tube at a space velocity (SV) of 1800 $h^{-1}$, and subjected to the oxidation reaction under the conditions of entrance pressure 0.22 MPa (absolute). The result was as shown in Table 3.

TABLE 1

| | Shaped Catalyst | Metallic Elementary Composition (atomic ratios Excluding Oxygen) | Content of Inert Component (%) | Shape and dimensions (outer diameter (mm) × inner diameter (mm) × height (mm)) | Occupation Volume (mm³) | Calcining Temp. (° C.) | Calcining Time (h) |
|---|---|---|---|---|---|---|---|
| Referential Example 1 | (1) | $Mo_{12}W_{0.5}Bi_1Fe_1Co_5Ni_3K_{0.1}$ | 0 | ring: 6 × 2 × 6 | 170 | 480 | 8 |
| Referential Example 2 | | BET specific surface area: 1 m²/g of alumina powder | 100 | ring: 6 × 2 × 6 | 170 | 480 | 8 |
| Referential Example 3 | (2) | $Mo_{12}W_{0.5}Bi_1Fe_1Co_5Ni_3K_{0.1}$ | 60 | ring: 6 × 2 × 6 | 170 | 500 | 8 |
| Referential Example 4 | (3) | $Mo_{12}W_{0.5}Bi_1Fe_1Co_5Ni_3K_{0.1}$ | 0 | ring: 6 × 2 × 6 | 170 | 500 | 8 |
| Referential Example 5 | (4) | $Mo_{12}W_{0.5}Bi_1Fe_1Co_5Ni_3Cs_{0.05}$ | 55 | ring: 6 × 2 × 6 | 170 | 480 | 8 |
| Referential Example 6 | (5) | $Mo_{12}W_{0.5}Bi_1Fe_1Co_5Ni_3Cs_{0.05}$ | 0 | ring: 6 × 2 × 6 | 170 | 480 | 8 |
| Referential Example 7 | (6) | $Mo_{12}W_{0.5}Bi_1Fe_1Co_5Ni_3K_{0.1}$ | 50 | ring: 9 × 2 × 9 | 572 | 480 | 8 |
| Referential Example 8 | (7) | $Mo_{12}W_{0.5}Bi_1Fe_1Co_5Ni_3K_{0.1}$ | 50 | ring: 6 × 2 × 6 | 170 | 480 | 8 |
| Referential Example 9 | (8) | $Mo_{12}W_{0.5}Bi_1Fe_1Co_5Ni_3Cs_{0.05}$ | 20 | ring: 6 × 2 × 6 | 170 | 500 | 8 |
| Referential Example 10 | (9) | $Mo_{12}W_{0.5}Bi_1Fe_1Co_5Ni_3Cs_{0.05}$ | 0 | ring: 6 × 2 × 6 | 170 | 500 | 8 |
| Referential Example 11 | (10) | $Mo_{12}W_{0.5}Bi_1Fe_1Co_5Ni_3Cs_{0.04}$ | 25 | ring: 8 × 2 × 8 | 402 | 480 | 8 |
| Referential Example 12 | (11) | $Mo_{12}W_{0.5}Bi_1Fe_1Co_5Ni_3Cs_{0.03}$ | 10 | ring: 7 × 2 × 7 | 269 | 490 | 8 |
| Referential Example 13 | (12) | $Mo_{12}W_{0.5}Bi_1Fe_1Co_5Ni_3K_{0.1}$ | 40 | ring: 9 × 2 × 9 | 572 | 500 | 8 |

Referential Example 14

The oxidation reaction as in Referential Example 1 was repeated, while replacing the shaped catalyst (1) with shaped catalysts (2)-(12) in each run. The results were as shown in Table 2.

TABLE 2

| | Shaped Catalyst | Propylene Conversion (mol %) | Selectivity for Acrolein and Acrylic Acid (mol %) | Yield of Acrolein and Acrylic Acid (mol %) |
|---|---|---|---|---|
| Referential Example 1 | (1) | 99.3 | 93.6 | 92.9 |
| Referential Example 2 | | — | — | — |
| Referential Example 3 | (2) | 83.4 | 95.3 | 79.5 |
| Referential Example 4 | (3) | 94.1 | 94.2 | 88.6 |
| Referential Example 5 | (4) | 81.5 | 95.8 | 78.1 |

Comparative Example 14

The oxidation reaction was conducted in the identical manner with Example 1, except that the shaped catalyst (2) was replaced with shaped catalyst (3). As indicated in Table 3, however, temperature at the hot spot rose drastically and the reaction could not be continued.

Examples 2–7 and Comparative Examples 2–4

The oxidation reaction of Example 1 was repeated except that the shaped catalyst (2) was replaced in each run with another catalyst as indicated in Table 3. The results were as shown in Table 3.

TABLE 3

|  | Kind (No.) and Amount (ml) of Shaped Catalyst Filled in Reaction Tube | | Reaction Temp. (° C.) | Hot Spot Temp. (° C.) | Propylene Conversion (mol %) | Selectivity for Acrolein and Acrylic Acid (mol %) | Yield of Acrolein and Acrylic Acid (mol %) |
|---|---|---|---|---|---|---|---|
|  | Reaction gas inlet side | Reaction gas outlet side |  |  |  |  |  |
| Example 1 | (2) 500 | (1) 1000 | 300 | 376 | 98.5 | 95.4 | 94.0 |
| Comparative Example 1 | (3) 500 | (1) 1000 | 300 | drastic rise | continuation of reaction impossible | | |
| Example 2 | (4) 500 | (1) 1000 | 300 | 379 | 98.6 | 95.3 | 94.0 |
| Comparative Example 2 | (5) 500 | (1) 1000 | 300 | drastic rise | continuation of reaction impossible | | |
| Example 3 | (6) 500 | (1) 1000 | 300 | 372 | 98.7 | 95.5 | 94.3 |
| Comparative Example 3 | (7) 500 | (1) 1000 | 300 | 417 | 98.5 | 90.9 | 89.5 |
| Example 4 | (8) 500 | (1) 1000 | 300 | 377 | 98.6 | 95.6 | 94.3 |
| Comparative Example 4 | (9) 500 | (1) 1000 | 300 | 413 | 98.3 | 91.5 | 89.8 |
| Example 5 | (10) 500 | (1) 1000 | 300 | 378 | 98.9 | 95.8 | 94.7 |
| Example 6 | (11) 500 | (1) 1000 | 300 | 375 | 99.1 | 96.0 | 95.1 |
| Example 7 | (12) 500 | (1) 1000 | 300 | 374 | 98.8 | 94.7 | 93.6 |

Example 8

The oxidation reaction of Example 6 was repeated except that the composition of the gaseous mixture was varied to propylene, 8 volume %; oxygen, 14 volume %; steam, 5 volume % and nitrogen-containing inert gas, 73 volume %. The results were: propylene conversion, 99.2%; selectivity for acrolein and acrylic acid, 96.2%; and yield of acrolein and acrylic acid, 95.4%.

What is claimed is:

1. A process for preparing unsaturated aldehydes and unsaturated carboxylic acids through vapor-phase catalytic oxidation of at least one starting compound selected from propylene, isobutylene, t-butanol and methyl-t-butyl ether with molecular oxygen or a molecular oxygen-containing gas, using a fixed bed shell-and-tube type reactor filled with shaped catalysts, which is characterized in that plural shaped catalysts exhibiting different activity levels are prepared by varying: [I] content of inert component of the shaped catalyst and [II] at least one of the factors (a) occupation volume of the shaped catalyst, (b) kind and/or amount of the alkali metal(s) in the shaped catalyst, and (c) calcining temperature of the shaped catalyst; and which catalysts are filled in each of the reaction tubes in such a manner that the catalytic activity level rises from the reactant gas-inlet side of each reaction tube toward the outlet side.

2. A process according to claim 1, in which the active component in the shaped catalyst is a complex oxide which is expressed by the following general formula (1):

$$Mo_aW_bBi_cFe_dA_eB_fC_gD_hO_x \qquad (1)$$

(wherein Mo is molybdenum; W is tungsten; Bi is bismuth; Fe is iron; A is at least an element selected from cobalt and nickel; B is at least an element selected from phosphorus, antimony, boron, tin, cerium, niobium, lead, chromium and zinc; C is at least an element selected from alkali metal elements; D is at least an element selected from alkaline earth metal elements; and O is oxygen; a, b, c, d, e, f, g, h and x stand for atomic numbers of Mo, W, Bi, Fe, A, B, C, D and O, respectively; where a is 12, b is 0–5, c is 0.1–10, d is 0.1–10, e is 1–20, f is 0–5, g is 0.001–3, h is 0–5, and x is a numerical value determined by the state of oxidation of each of the elements).

3. The process according to claim 1, in which the inert component in the shaped catalyst is an inert substance having a BET specific surface area not exceeding 20 $m^2/g$.

4. The process according to claim 2, in which the inert component in the shaped catalyst is an inert substance having a BET specific surface area not exceeding 20 $m^2/g$.

* * * * *